(12) United States Patent
Casas-Ganem et al.

(10) Patent No.: US 11,000,378 B2
(45) Date of Patent: May 11, 2021

(54) ACETABULAR SURGICAL IMPLANT FOR SEGMENTAL PELVIC DEFECT AND METHODS OF USE AND MANUFACTURE

(71) Applicant: Surgical Device Innovations, LLC, Dallas, TX (US)

(72) Inventors: Jorge Casas-Ganem, Dallas, TX (US); Joshua Haney, Frisco, TX (US)

(73) Assignee: Surgical Device Innovations, LLC, Dallas, TX (US)

( * ) Notice: Subject to any disclaimer, the term of this patent is extended or adjusted under 35 U.S.C. 154(b) by 0 days.

(21) Appl. No.: 15/431,952

(22) Filed: Feb. 14, 2017

(65) Prior Publication Data

US 2018/0228615 A1 Aug. 16, 2018

(51) Int. Cl.
*A61F 2/34* (2006.01)
*A61F 2/30* (2006.01)

(52) U.S. Cl.
CPC ............ *A61F 2/34* (2013.01); *A61F 2/30771* (2013.01); *A61F 2002/30245* (2013.01); *A61F 2002/30736* (2013.01); *A61F 2002/30784* (2013.01); *A61F 2002/30828* (2013.01); *A61F 2002/30878* (2013.01); *A61F 2002/30884* (2013.01); *A61F 2002/3401* (2013.01); *A61F 2002/3412* (2013.01)

(58) Field of Classification Search
CPC ...... A61F 2002/3401; A61F 2002/3412; A61F 2/34
See application file for complete search history.

(56) References Cited

U.S. PATENT DOCUMENTS

| | | | | | |
|---|---|---|---|---|---|
| 3,528,109 | A | * | 9/1970 | Scales | A61F 2/30724 623/22.38 |
| 3,685,058 | A | * | 8/1972 | Tronzo | A61F 2/32 623/22.15 |
| 3,808,606 | A | * | 5/1974 | Tronzo | A61C 8/0012 428/220 |
| 3,840,904 | A | * | 10/1974 | Tronzo | A61F 2/30767 623/22.32 |

(Continued)

OTHER PUBLICATIONS

Stanmore Implants; METS Coned Hemi-Pelvis; brochure; Copyright 2010.

(Continued)

*Primary Examiner* — Bruce E Snow
*Assistant Examiner* — Melissa A Hoban
(74) *Attorney, Agent, or Firm* — Polsinelli PC; Adam C. Rehm

(57) ABSTRACT

A medical device, i.e., an acetabular surgical implant, for a segmental acetabular defect with pelvic discontinuity that is installable and fully functional without any need for any intermediary implant such as a surgical cage or a surgical shell. The surgical implant includes a hemispherical cup with a plurality of equidistant apertures extending through the cup, and a ribbed, elongated stress-diffusion element, i.e., a stem, extending from the cup. The stem is formed to extend from and be oriented with respect to the cup based on whether the surgical implant is to be used on a left side of the patient, i.e., a left acetabulum, or a right side of the patient, i.e., a right acetabulum, for reconstruction of the segmental acetabular defect.

19 Claims, 15 Drawing Sheets

(56) References Cited

U.S. PATENT DOCUMENTS

| | | | | |
|---|---|---|---|---|
| 4,769,041 A | * | 9/1988 | Morscher | A61F 2/30721 623/22.33 |
| 4,828,565 A | * | 5/1989 | Duthoit | A61F 2/30767 623/22.3 |
| 4,840,632 A | * | 6/1989 | Kampner | A61B 17/1666 623/22.36 |
| 4,936,856 A | * | 6/1990 | Keller | A61F 2/30721 623/22.36 |
| 4,955,919 A | * | 9/1990 | Pappas | A61F 2/34 623/22.26 |
| 5,049,158 A | | 9/1991 | Englehardt | |
| 5,108,446 A | * | 4/1992 | Wagner | A61F 2/34 623/22.26 |
| 5,171,285 A | | 12/1992 | Broderick | |
| 5,211,665 A | * | 5/1993 | Ku | A61F 2/30721 623/22.38 |
| 5,549,691 A | * | 8/1996 | Harwin | A61F 2/30744 623/22.34 |
| 5,653,765 A | * | 8/1997 | McTighe | A61F 2/36 623/18.11 |
| 5,658,347 A | | 8/1997 | Sarkisian | |
| 5,725,594 A | * | 3/1998 | McTighe | A61F 2/3662 623/23.21 |
| 5,904,688 A | | 5/1999 | Gilbert | |
| 5,938,702 A | | 8/1999 | Lopez | |
| 6,332,896 B1 | * | 12/2001 | Hubbard | A61F 2/3662 623/23.24 |
| 7,255,712 B1 | * | 8/2007 | Steinberg | A61B 17/7208 606/63 |
| 7,267,693 B1 | | 9/2007 | Mandell | |
| 7,597,715 B2 | * | 10/2009 | Brown | A61F 2/34 623/22.12 |
| D618,800 S | | 6/2010 | Mayon | |
| 8,308,811 B2 | | 11/2012 | Newsome | |
| 8,372,155 B2 | | 2/2013 | Tuke | |
| 8,641,771 B2 | | 2/2014 | Caylor | |
| 8,900,321 B2 | * | 12/2014 | Weiss | A61B 17/686 623/22.32 |
| 9,144,497 B2 | | 9/2015 | Sun | |
| 9,180,013 B2 | | 11/2015 | Grostefon | |
| 9,220,599 B2 | | 12/2015 | Meridew | |
| 9,248,023 B2 | * | 2/2016 | Ries | A61F 2/30721 |
| 9,308,102 B2 | | 4/2016 | McCarthy | |
| D765,845 S | | 9/2016 | Prybyla | |
| 9,820,853 B2 | | 11/2017 | Meridew | |
| 9,820,854 B2 | | 11/2017 | Preuss | |
| 9,931,213 B2 | | 4/2018 | Sartawi | |
| 9,987,148 B2 | | 6/2018 | Li | |
| 2005/0234559 A1 | * | 10/2005 | Fernandez | A61F 2/36 623/23.21 |
| 2013/0131823 A1 | * | 5/2013 | Morrey | A61F 2/34 623/22.24 |
| 2017/0202671 A1 | * | 7/2017 | Ries | A61F 2/4637 |

OTHER PUBLICATIONS

Fiorenza, Fabrice; Indications and treatments for partial pelvic defects: pedestal cups; Arthroplasty Disaster Conference; PowerPoint presentation dated Sep. 21-23, 2016.

Implantcast GMBH; MUTARS LUMiC Surgical Technique; brochure dated Jun. 2016.

* cited by examiner

ACETABULAR SURGICAL IMPLANT FOR SEGMENTAL PELVIC DEFECT AND METHODS OF USE AND MANUFACTURE

BACKGROUND OF THE INVENTION

1. Field of the Invention

The present inventive concept relates generally to medical devices, and more particularly, to an acetabular surgical implant for a segmental pelvic defect and methods of use and manufacture.

2. Description of the Related Art

Loss of acetabular bone with distortion of anatomical pelvic landmarks pose a challenge to orthopedic surgeons. Conventional reconstructive medical devices designed to address such have a number of limitations and are inadequate. Among other deficiencies, such conventional reconstructive medical devices are modular and require a plurality of different devices and other materials, e.g., cement and/or cadaver bone, which is undesirable and suffer from high failure rates. Failure of an implant is often catastrophic given such results in unnecessary pain and costs to a patient, and may even result in death depending on various circumstances associated with the failure.

For instance, FIGS. 12 and 13 illustrate a conventional reconstructive medical device assembly 120 used in two different procedures where varying degrees of bone 122 from a patient has been exposed and/or removed. The conventional reconstructive medical device assembly 120 includes a cage 124 having a body 126 with three flanges 128 that allow fixation of screws 130 to intact portion of the bone 122. The conventional reconstructive medical device assembly 120 further includes an acetabular shell 132 adhered to the cage 124 via cement 134. The design of the conventional reconstructive medical device assembly 120 does not allow growth of the bone 122 in and/or around the conventional reconstructive medical device assembly 120. As such, the conventional reconstructive medical device assembly 120 is never incorporated into the bone 122, which results in a high failure rate due to fatigue of the conventional reconstructive medical device assembly 120. Also, in the procedure illustrated by FIG. 13, extensive stripping of the hip abductor muscles from the outer portion of the pelvis must be performed in order to place the flanged cage construct. Such extensive soft tissue exposure permanently weakens the hip abductor muscles resulting in a permanent limp and an increased risk of dislocation of the prosthetic hip. Further, one of the three flanges 128 must be cut off due to an absence of bone inferiorly, which results in unnecessary waste.

FIGS. 14 and 15 illustrate another conventional reconstructive medical device assembly 140 used in two different procedures where varying degrees of bone 142 from a patient has been exposed and/or removed. The conventional reconstructive medical device assembly 140 includes a wedge or augment 144 fixed to an intact portion of the bone 142 with screws 146. The conventional reconstructive medical device assembly 140 also includes a body 148 that must be anchored to the augment 144 via cement 152. The use of a plurality of implants secured together and to the bone 142 in such a manner causes the conventional reconstructive medical device assembly 140 to have a high failure rate due to micromotion between the augment 144 and the body of the acetabular shell 148. Further, in the procedure illustrated by FIG. 15, the failure rate is particularly high due to an absence of bone available to grow around the conventional reconstructive medical device assembly 140.

Accordingly, there is a need for a reconstructive medical device that does not suffer from the limitations of conventional reconstructive medical devices, does not allow forces to be transmitted between multiple implants, is readily accepted by surrounding bone, allows growth of bone in and around the device, has a simple design that is easy to use, has a reproducible technique for implantation, minimizes surgical exposure and stripping of the bone, and does not prolong recovery time or expenses of a patient, and does not increase the risk of repeat revision surgery.

SUMMARY OF THE INVENTION

The following brief description is provided to indicate the nature of the subject matter disclosed herein. While certain aspects of the present inventive concept are described below, the summary is not intended to limit the scope of the present inventive concept. Embodiments of the present inventive concept provide an inventive concept for a medical device, and a method of using such medical device for a segmental pelvic defect during a surgical procedure. The present inventive concept does not suffer from and remedies the deficiencies of conventional devices such as those previously set forth herein.

The present inventive concept provides, in its simplest form, an implantable medical device having a hemispherical cup with a plurality of equidistant apertures extending through the cup, and a ribbed, elongated stress-diffusion element, i.e., a stem, extending from the cup. The device may have one or more apertures. The apertures may be arranged in an array or a non-equidistant pattern, or a random pattern or a clustered pattern. An internal surface of one or more of the apertures may be variably angled so that the respective one or more of the apertures has a cone shape, allowing optimal screw placement into bone depending on the configuration of the acetabular defect. The cup and stem are operable to be mounted directly on and to a user's pelvis, thereby preventing any motion therebetween while allowing the medical device to directly transfer stress to bone of the user. The direct transfer of stress to the bone of the user causes the bone immediately adjacent to the medical device to grow stronger. Additionally, the direct placement of the medical device on the bone of the user enhances the ability of the bone of the user to incorporate or grow into and/or around the medical device. In this manner, the medical device of the present inventive concept provides increased functionality relative to conventional medical implants.

An object of the present inventive concept is to provide a one-piece, unitary medical device for surgical implantation to remedy a segmental pelvic defect that is installable and fully functional without any additional implants or other pieces other than a limited number of optional surgical placement screws, i.e., zero screws, one screw, two screws, three screws, or four screws, which may be installed to extend partially through the medical device and into one or more bones of the user.

Another object of the present inventive concept is to provide a medical device, e.g., an acetabular implant, for a pelvic defect that is installable and fully functional without any need for a surgical cage, a surgical shell, or any other intermediary implant, part, or material, e.g., an adhesive or cadaver bone which has a high-infection rate, positioned between the medical device and bone of the user.

Another object of the present inventive concept is to provide a medical device for pelvis reconstruction, e.g., in a revision hip replacement or a pelvic tumor resection, that receives stress from movement of the user, e.g., walking, and redistributes the stress along an extended portion of the user, e.g., one or more bones of the user.

Another object of the general inventive concept is to provide a surgical implant that is easy to use, comparatively simple to manufacture, and especially well adapted for the intended usage thereof.

The aforementioned objects and advantages of the present inventive concept may be achieved by providing a medical device or surgical implant. The implant may include a hemispherical cup having (i) a bone-abutment exterior surface, (ii) an interior surface defining a cavity, and/or (iii) a circumferential rim extending between the exterior surface and the interior surface. The implant may include at least one aperture extending between the exterior surface and the interior surface. The implant may include a stress-diffusion element extending from the cup. The cup and the stress-diffusion element are formed from a single block, e.g., a monoblock, thereby providing an implant consisting of a unitary piece.

The rim may extend entirely along only a single plane. The rim may define a circle with a first center point, i.e., an imaginary center point, at a center thereof. The exterior surface of the cup may define a second center point at a center thereof relative to a perimeter edge defined by the rim. A line, i.e., an imaginary line drawn, between the first center point and the second center point extends perpendicular to the plane.

The stress-diffusion element may be an elongated stem extending from the cup. The stem may include an intermediary base between the stem and the cup and may provide rotational stability by preventing rotation of the implant relative to a hole or bone tunnel in which the implant is installed. The base may be formed on the exterior surface of the cup and spaced from the second center point. The base may be centered between the second center point and a closest portion of the rim. The base may be centered between the at least one aperture and another aperture extending between the exterior surface and the interior surface.

The stress-diffusion element may include a plurality of longitudinal flutes. The stress-diffusion element may be smooth without any longitudinal flutes. Each of the plurality of longitudinal flutes may extend along an entirety of or a substantial portion of the stress-diffusion element. Each of the plurality of longitudinal flutes extend along an entirety of the stem. In this manner, the stem is a fluted stem. Distal ends of the plurality longitudinal flutes may adjoin at a common point. Individual proximal ends of the plurality longitudinal flutes may taper at individual, separate points. Adjacent ones of the plurality of longitudinal flutes may be spaced from each other by a trough with sidewalls and a bottom wall. One or more of the plurality of longitudinal flutes may not include a bottom wall, with the sidewalls adjoining each other. Each of the troughs may include an increasing depth along the stem. Each of the plurality of longitudinal flutes may include an increasing width along the stem. Ends of each of the plurality of longitudinal flutes may partially surround a portion of adjacent ones of the trough. Each of the plurality of longitudinal flutes may include a plateau along at least a portion thereof. Each of the plateaus may have an increasing width along the stem. The sidewalls of each of troughs may converge. A distance between sidewalls of each of the troughs may increase/decrease along a distance thereof. The at least one aperture may include a set of apertures or two sets of apertures, i.e., four apertures, arranged equidistant relative to each other along the cup. The rim may include a plurality of indentations arranged equidistant relative to each other along the rim.

The aforementioned objects and advantages of the present inventive concept may further be achieved by providing a surgical method of implanting a medical device. The method may include the step of exposing a portion of a bone of a patient. The method may include the step of forming a bone tunnel or hole at least partially through a bone of a patient. The method may include the step of placing a medical device on the bone so that a portion of the medical device extends at least partially into the bone tunnel, with the portion of the medical device in direct contact with the bone so that force can be efficiently transferred from the portion of the medical device to the bone or otherwise distributed or shared between the medical device and/or the bone of the patient. The medical device may be secured in the bone tunnel via a friction-fit engagement. The method may include hammering the medical device so that a portion of the medical device extends into a bone of the patient. A hole or bone tunnel may or may not be formed to receive the portion of the medical device. The medical device may include a hemispherical cup having a bone-abutment exterior surface, an interior surface defining a cavity, a circumferential rim extending between the exterior surface and the interior surface, and/or at least one aperture extending between the exterior surface and the interior surface. The medical device may include a stress-diffusion element extending from the cup.

The method may include the step of securing the medical device to the bone by installing a bone screw partially through the at least one aperture and into the bone. The placing of the medical device on the bone may include orienting the medical device so that (i) the cup is directly on the bone, and/or (ii) a substantial portion of the stress-diffusion element is directly on and extending along the bone so that stress received by the medical device is diffused through the medical device and distributed along the stress-diffusion element. The medical device may be secured to the bone without any other devices, adhesives, or other element.

The stress-diffusion element may include a plurality of longitudinal flutes. Each of the plurality of longitudinal flutes may extend along an entirety of the stem with (i) distal ends of the plurality longitudinal flutes adjoining at a common point, and/or (ii) proximal ends of the plurality longitudinal flutes tapering at separate points.

The aforementioned objects and advantages of the present inventive concept may further be achieved by providing a method of forming a medical device. The method may include the step of forming a hemispherical cup having (i) a bone-abutment exterior surface, (ii) an interior surface defining a cavity, (iii) a circumferential rim extending between the exterior surface and the interior surface, and/or (iv) a stress-diffusion element extending from the cup. The method may include the step of forming at least one aperture through the exterior surface and the interior surface. The cup and the stress-diffusion element may be co-formed from a single block or piece of material, i.e., a mono block. The cup and the stress-diffusion element may be formed as a unitary piece. The method may not include a step of attaching the stress-diffusion element to the cup.

The foregoing and other objects are intended to be illustrative of the present inventive concept and are not meant in a limiting sense. Many possible embodiments of the present inventive concept may be made and will be readily evident upon a study of the following specification and accompanying drawings comprising a part thereof. Various features and subcombinations of the present inventive concept may be employed without reference to other features and subcombinations. Other objects and advantages of this present inventive concept will become apparent from the following description taken in connection with the accompanying drawings, wherein is set forth by way of illustration and example, an embodiment of this present inventive concept and various features thereof.

BRIEF DESCRIPTION OF THE DRAWINGS

A preferred embodiment of the present inventive concept, illustrative of the best mode in which the applicant has contemplated applying the principles, is set forth in the following description and is shown in the drawings.

DETAILED DESCRIPTION OF THE PREFERRED EMBODIMENTS

Figure 1:
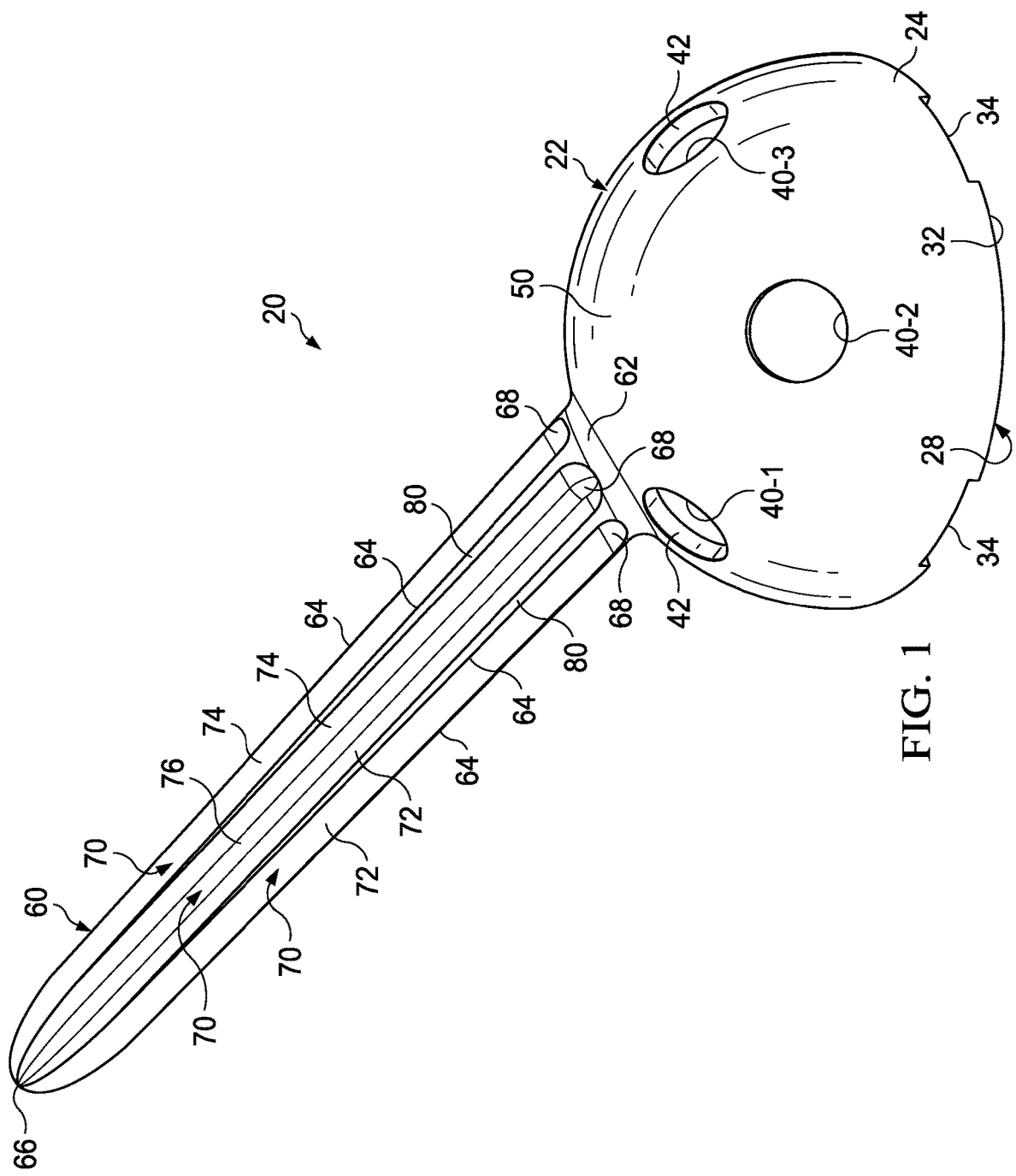
FIG. 1 is a top, left rear perspective view of a medical device, i.e., a surgical acetabular implant of the present inventive concept.

The following detailed description of the present inventive concept references the accompanying drawings that illustrate specific embodiments in which the present inventive concept can be practiced. The embodiments are intended to describe aspects of the present inventive concept in sufficient detail to enable those skilled in the art to practice the present inventive concept. Other embodiments can be utilized and changes can be made without departing from the scope of the present inventive concept. The following detailed description is, therefore, not to be taken in a limiting sense. The scope of the present inventive concept is defined only by the appended claims, along with the full scope of equivalents to which such claims are entitled.

In this description, references to "one embodiment," "an embodiment," or "embodiments," mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, or the like described in one embodiment may also be included in other embodiments, but is not necessarily included. Thus, the present technology can include a variety of combinations and/or integrations of the embodiments described herein.

Turning to the drawings and particularly FIGS. 1-8, a medical device, i.e., a surgical acetabular implant 20 is illustrated. The surgical implant 20 includes a hemispherical cup 22 with an exterior surface 24, an interior surface 26, and a circumferential rim 28 extending between the surfaces 24, 26 and defining an outermost edge of the cup 22.

The exterior surface 24 is convex and provides a surface operable to abuttingly engage one or more bones of a patient when the surgical implant 20 is installed and in use. The interior surface 26 is concave and defines a cavity 30 provides a surface operable to abuttingly engage one or more other medical devices. The circumferential rim 28 defines a planar circle with a center point. The circumferential rim 28 has a plurality of indentations, which cause the circumferential rim 28 to have plurality of extensions 32 and a plurality of notches 34 alternately and evenly spaced about the circumferential rim 28. The plurality of extensions 32 and the plurality of notches 34 cause the circumferential rim 28 to have a variable, non-uniform surface, which advantageously provides a plurality of contact points to facilitate handling of the surgical implant 20 by an orthopedic surgeon during a surgical procedure. Additionally, the plurality of contact points facilitates mating of the surgical implant 20 with one or more other medical devices. It is foreseen, however, that the circumferential rim 28 could have a uniform surface with no notches or extensions without deviating from the scope of the present inventive concept.

Figure 5:
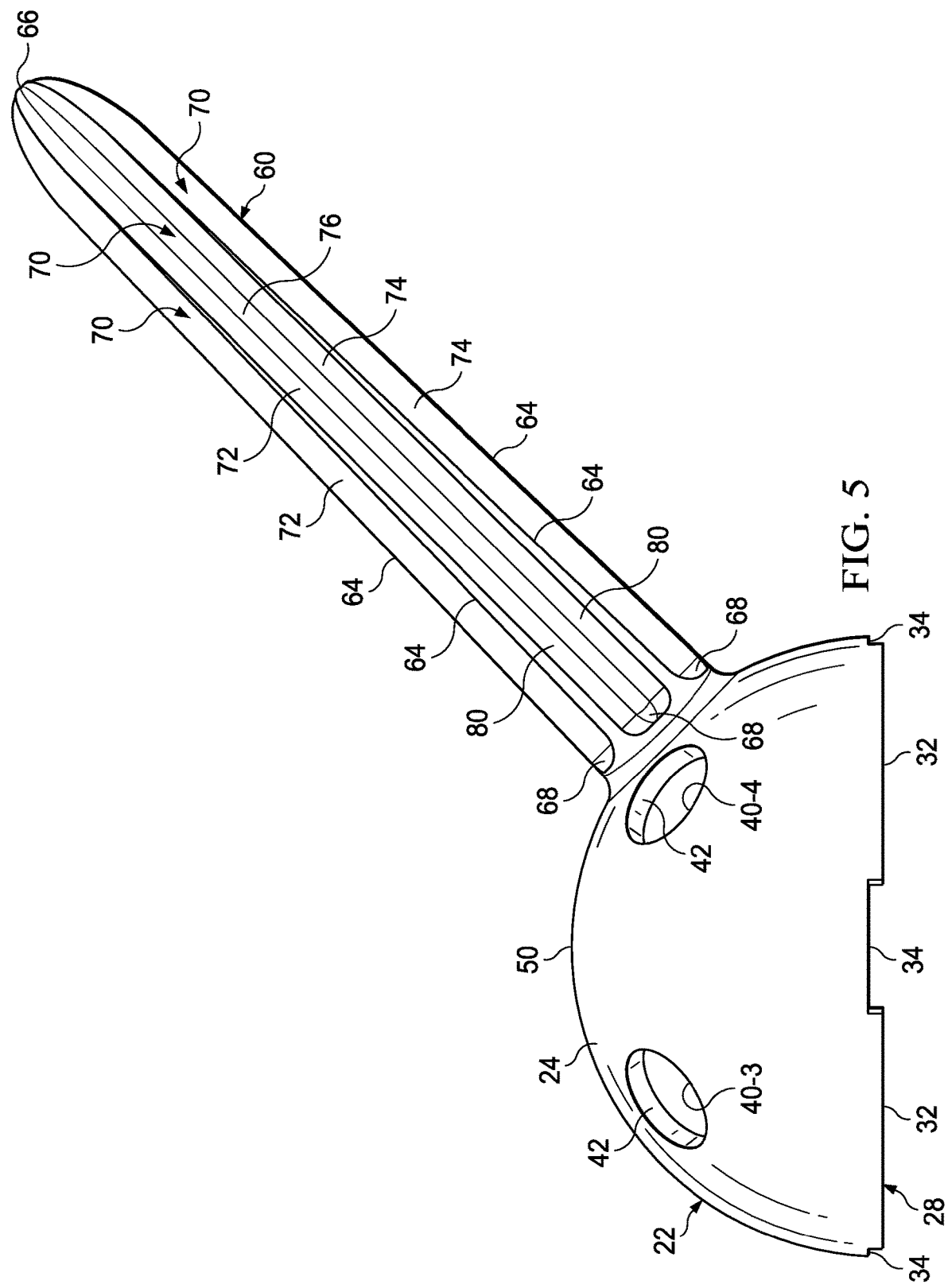
FIG. 5 is a right side elevation view of the surgical implant of FIG. 1.

The surgical implant 20 includes at least one aperture 40 extending through the cup 22 with an interior, circumferential surface 42 formed between the surfaces 24, 26 of the cup 22. In the exemplary embodiment, the surgical implant 20 includes four of the apertures 40, i.e., a first aperture 40-1, a second aperture 40-2, a third aperture 40-3, and a fourth aperture 40-4, evenly spaced around a perimeter of the cup 22. The perimeter is of a set distance between the outermost edge of the cup 22 defined by the circumferential rim 28, which is on one side of the cup 22, and an outermost center point 50 of the cup 22, which is on an opposite side of the cup 22. An imaginary line extending between the center point 50 and the center point defined by the rim 28 is perpendicular to the plane defined by the rim 28. As best illustrated by FIG. 5, each of the apertures 40 is spaced equidistant from each other around the perimeter of the cup, and are equally spaced from the center point 50. It is foreseen that the surgical implant 20 may include only one, two, or three of the apertures 40 without deviating from the scope of the present inventive concept. For instance, it is foreseen that the surgical implant 20 may only include the aperture 40-1 and/or the aperture 40-4 without deviating from the scope of the present inventive concept.

The surgical implant 20 includes an elongated stress-diffusion element or stem 60 extending from the exterior surface 24 of the cup 22. In the exemplary embodiment, the stem 60 is cylindrical and tapered, but it is foreseen that the stem 60 may be of one or more other shapes, e.g., rectangular and/or cylindrical, and/or be non-tapered with a uniform width without deviating from the scope of the present inventive concept.

The stem 60 includes a base 62 formed on the exterior surface 24 of the cup 22 and is spaced from the center point 50. The base 62 is centered between the center point 50 and a closest portion of the circumferential rim 28. The base 62 is centered between the apertures 40-1, 40-4. The stem 60 includes a plurality of longitudinal flutes 64. In the exemplary embodiment, the stem 60 includes six longitudinal flutes evenly spaced around the stem 60, but it is foreseen that the stem 60 may include (i) fewer longitudinal flutes, e.g., one rib, two, three, four, or five longitudinal flutes, (ii) additional longitudinal flutes, e.g., seven, eight, nine, or ten longitudinal flutes, or (iii) no longitudinal flutes without deviating from the scope of the present inventive concept. Each of the plurality of longitudinal flutes 64 extend along at least a substantial portion of the stem 60 and preferably along an entirety of the stem 60. Distal ends of each of the plurality of longitudinal flutes 64 meet at a common point 66, which defines an outermost point of the stem 60. Proximal ends of the plurality of longitudinal flutes 64 are tapered to separate points 68, which are adjacent to the base 62.

Adjacent ones of the plurality of longitudinal flutes 64 are spaced from each other by a trough 70 with sidewalls 72, 74 and a bottom wall 76. Each of the troughs 70 has an increasing depth in a direction from the point 66 toward its respective one of the points 68 along the stem 60. Each of the sidewalls 72, 74 of the troughs 70 converge in a direction from the point 66 toward its respective one of the points 68 along the stem 60. Each of the troughs 70 has an increasing width in a direction from the point 66 toward its respective one of the points 68 along the stem 60. Each of the plurality of longitudinal flutes 64 includes a plateau 80 along a portion thereof. Each of the plateaus 80 includes a width that increases in a direction from the point 66 toward its respective one of the points 68 along the stem 60. Each of the plurality of longitudinal flutes 64 includes an end portion that partially surrounds adjacent troughs 70 on each side of a respective one of the plurality of longitudinal flutes 64. End portions of adjacent ones of the plurality of longitudinal flutes 64 cooperatively surround an entire end of each of the troughs 70 formed therebetween.

The surgical implant 20 is operable to be surgically implanted into a patient to correct a pelvic defect. For instance, after a portion of a pelvic bone 90 of a patient has been exposed by the surgeon during a surgical procedure, a bone tunnel 92 is formed at least partially through the bone 90. In the exemplary embodiment, the bone tunnel 92 is formed by reaming via a reaming tool to have a depth that is equal to a length of the stem 60, and a tapered width that is equal to a width defined by the bottom wall 76 of the troughs 70 of the stem 60. Alternatively, it is also foreseen that the width of the bone tunnel 92 may be greater or less than the width defined by the bottom wall 76 of the troughs 70 of the stem 60 and/or not tapered without deviating from the scope of the present inventive concept. For instance, the bone tunnel 92 may be ¾ mm smaller than an outermost circumference of the stem 60. Alternatively, it is foreseen that the width of the bone tunnel 92 may be greater than, less than, or equal to the width of an outermost portion of the plurality of longitudinal flutes 64 of the stem 60 and/or tapered to correspond to the plurality of longitudinal flutes 64 of the stem 60 without deviating from the scope of the present inventive concept. It is foreseen that the depth of the bone tunnel 92 may be greater or less than the length of the stem 60 without deviating from the scope of the present inventive concept.

Figure 9:
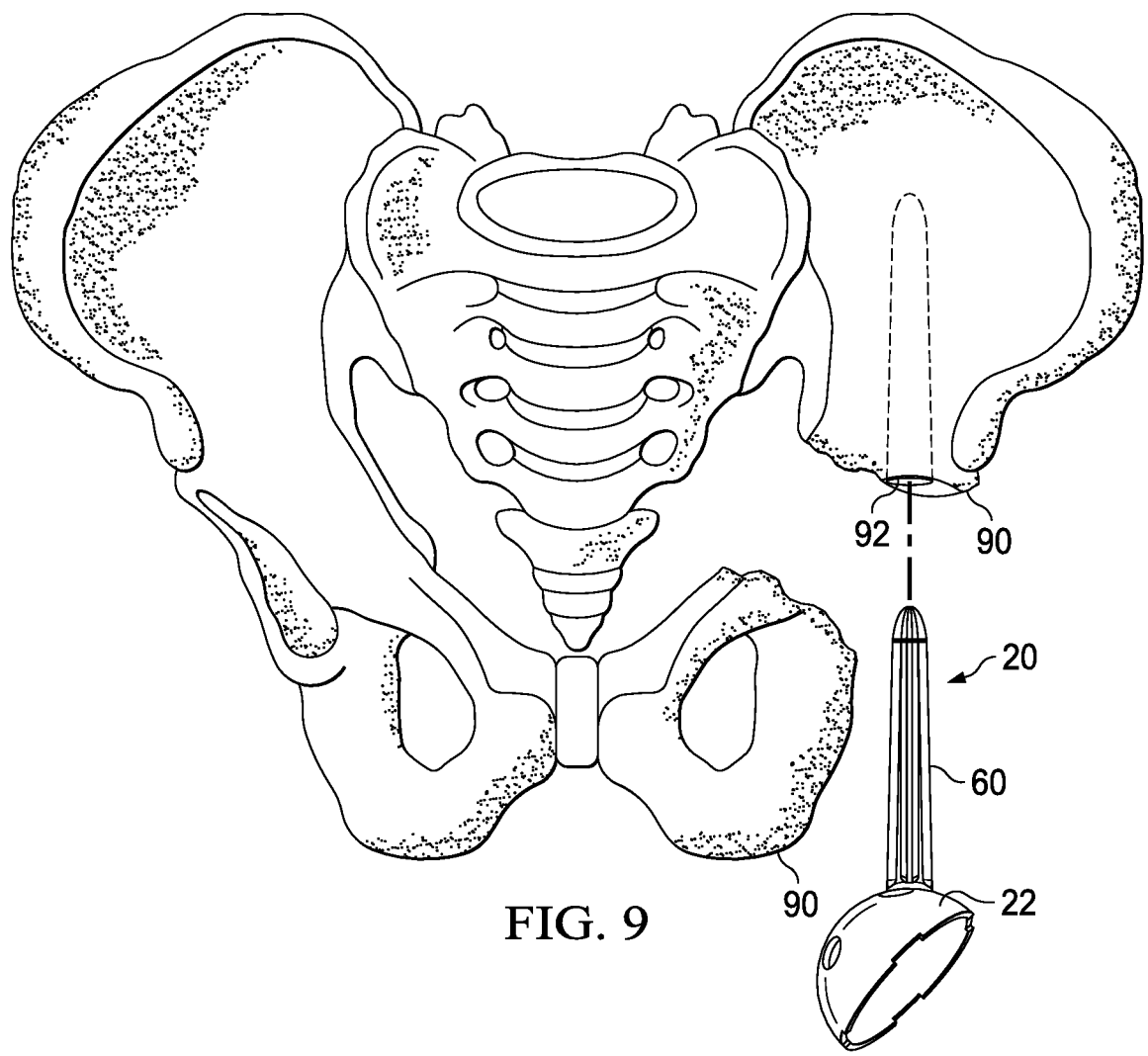
FIG. 9 is a diagram illustrating the surgical implant of FIG. 1 pre-installation into a tunnel formed in bone of a patient during use by an orthopedic surgeon during a surgical procedure.

After formation of the bone tunnel 92, the surgical implant 20 is positioned so that the stem 60 is aligned with the bone tunnel 92 as illustrated by FIG. 9. Next, the stem 60 is inserted into the bone tunnel 92 so that the surgical implant 20 is secured to the bone 90. It is foreseen that, depending on specific surgical applications, which may vary from patient to patient, the surgeon will likely be required to utilize a tool, e.g., a hammer, to force the stem 60 of the surgical implant 20 into the bone tunnel 92. For instance, if the bone tunnel 92 is formed to have a width equal to the width defined by the bottom wall 76 of the troughs 70 of the stem 60, then it will be necessary for the surgeon to force the surgical implant 20 into the bone tunnel 92 so that the plurality of longitudinal flutes 64 form grooves in the bone tunnel 92. In this manner, the plurality of longitudinal flutes 64 prevent the surgical implant 20 from rotating relative to the bone tunnel 92 after the surgical implant 20 has been installed in the bone 90.

Figure 10:
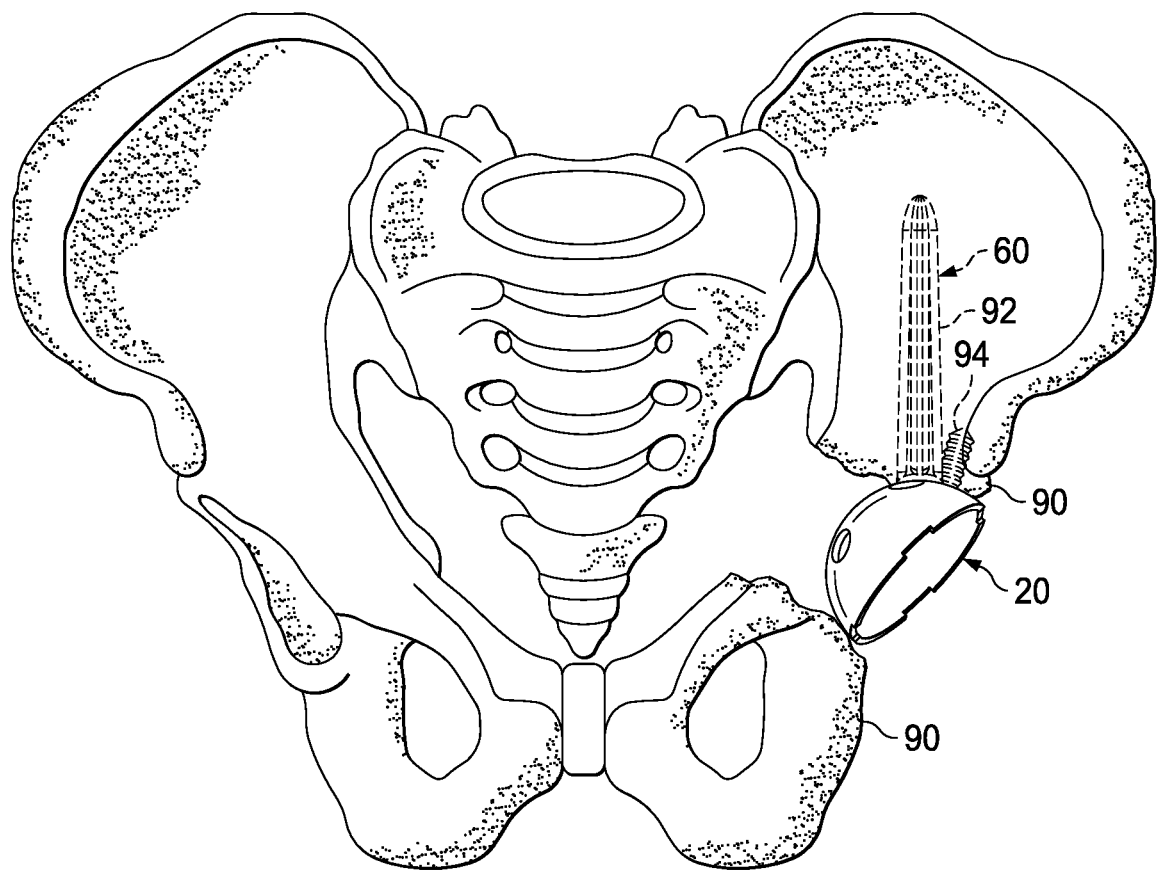
FIG. 10 is a diagram illustrating the surgical implant of FIG. 1 installed into the tunnel of FIG. 9.
Figure 11:
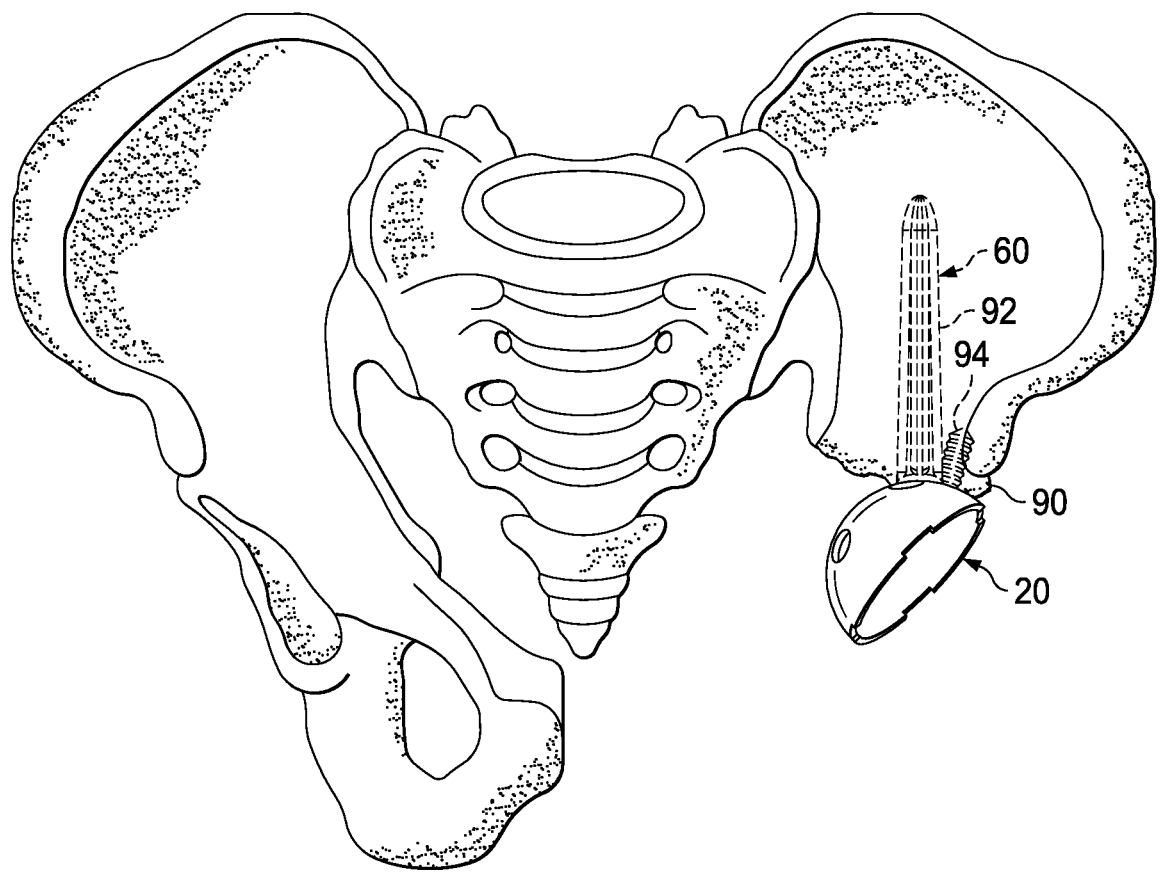
FIG. 11 is a diagram illustrating the surgical implant of FIG. 1 installed into a tunnel formed in bone of a patient during another surgical procedure.
Figure 12:
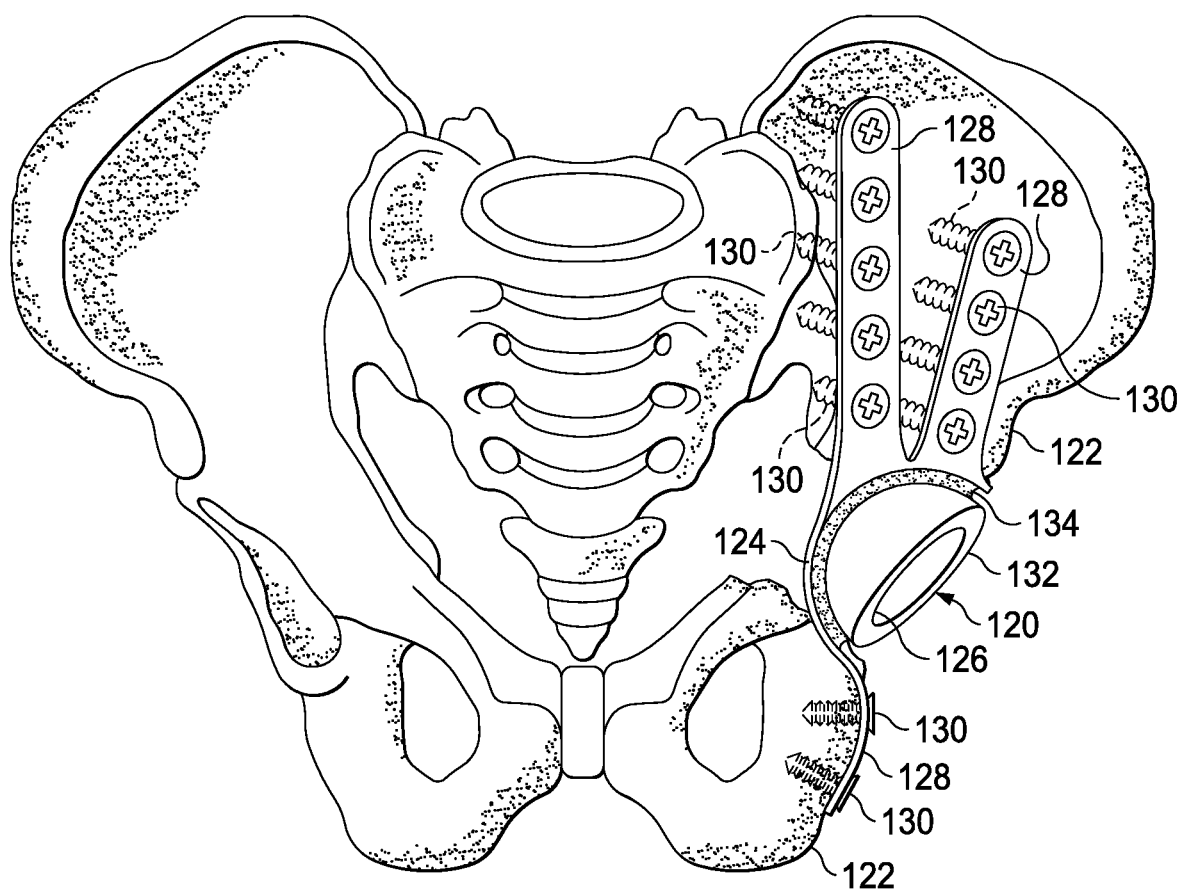
FIG. 12 is a diagram illustrating a plurality of conventional medical devices secured to bone of a patient.
Figure 13:
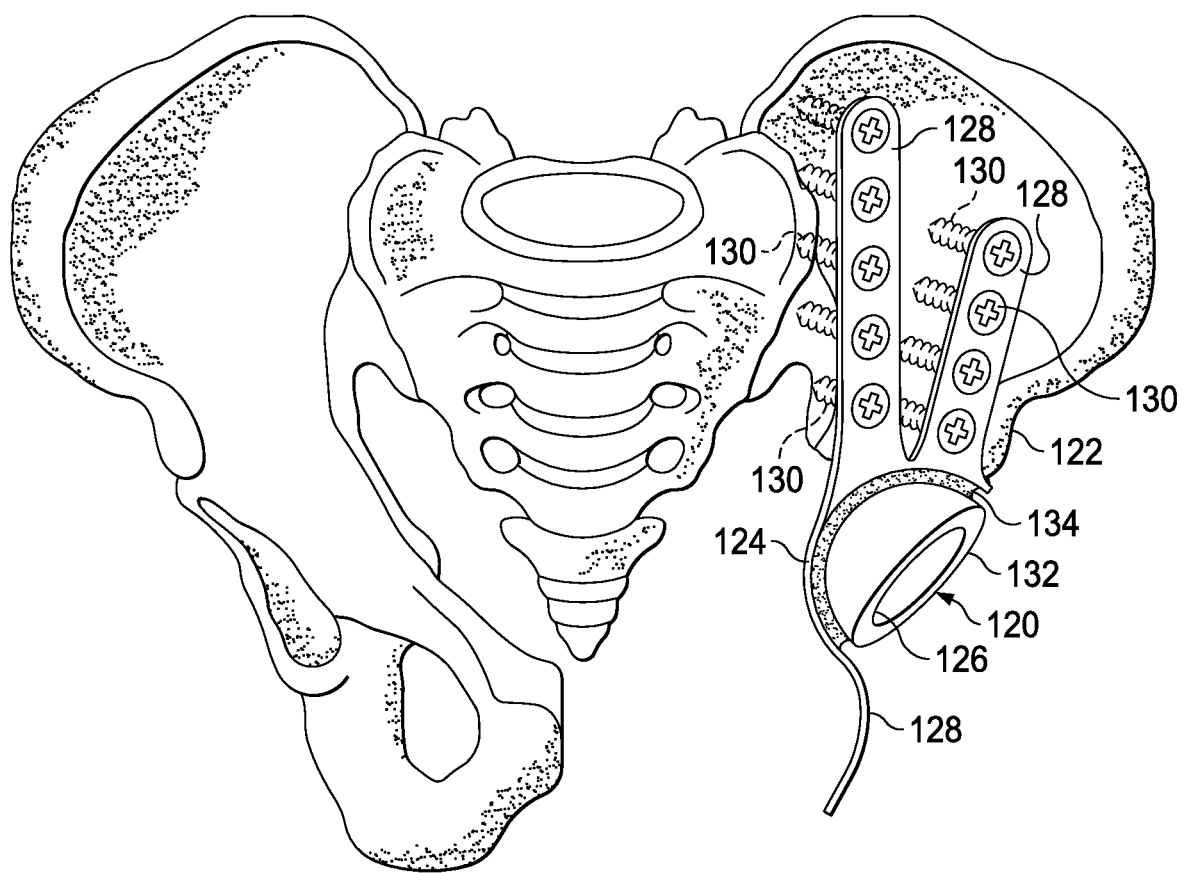
FIG. 13 is a diagram illustrating a plurality of conventional medical devices secured to bone of a patient.
Figure 14:
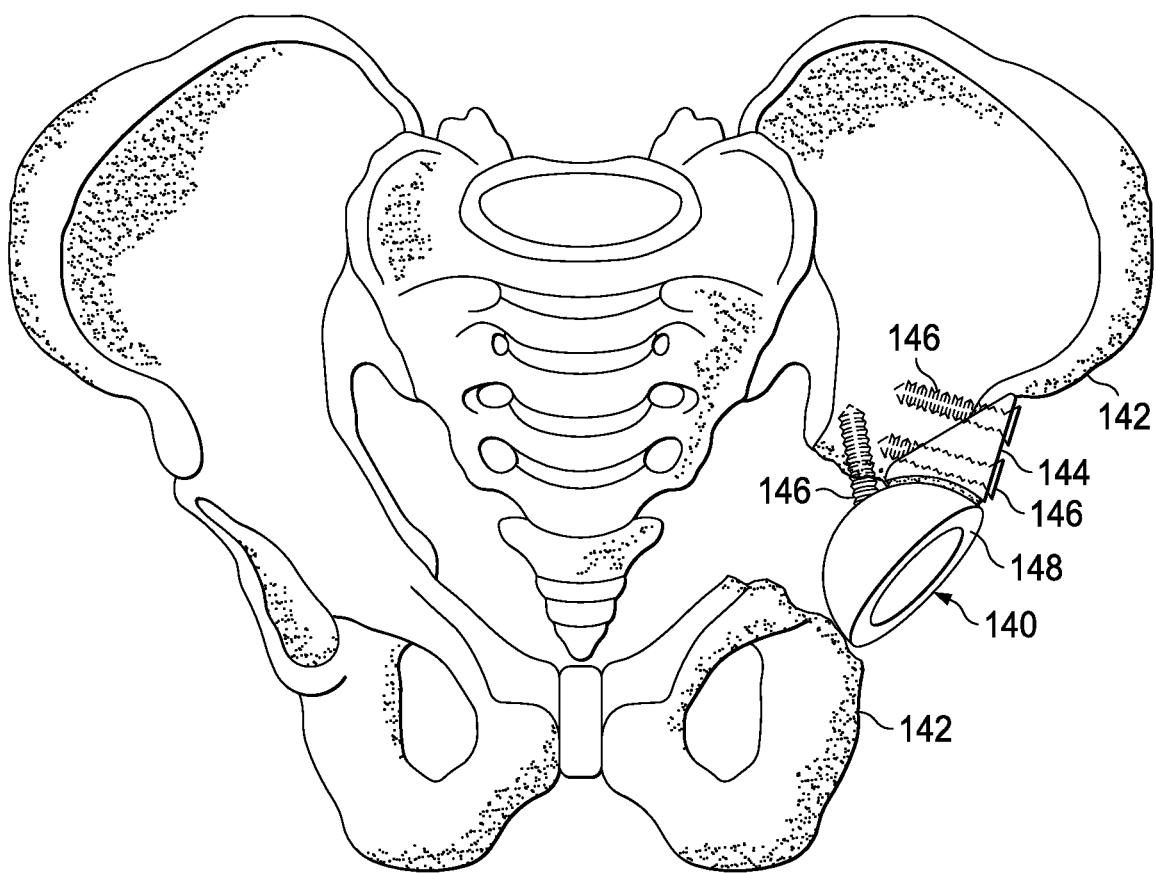
FIG. 14 is a diagram illustrating a plurality of conventional medical devices secured to bone of a patient.
Figure 15:
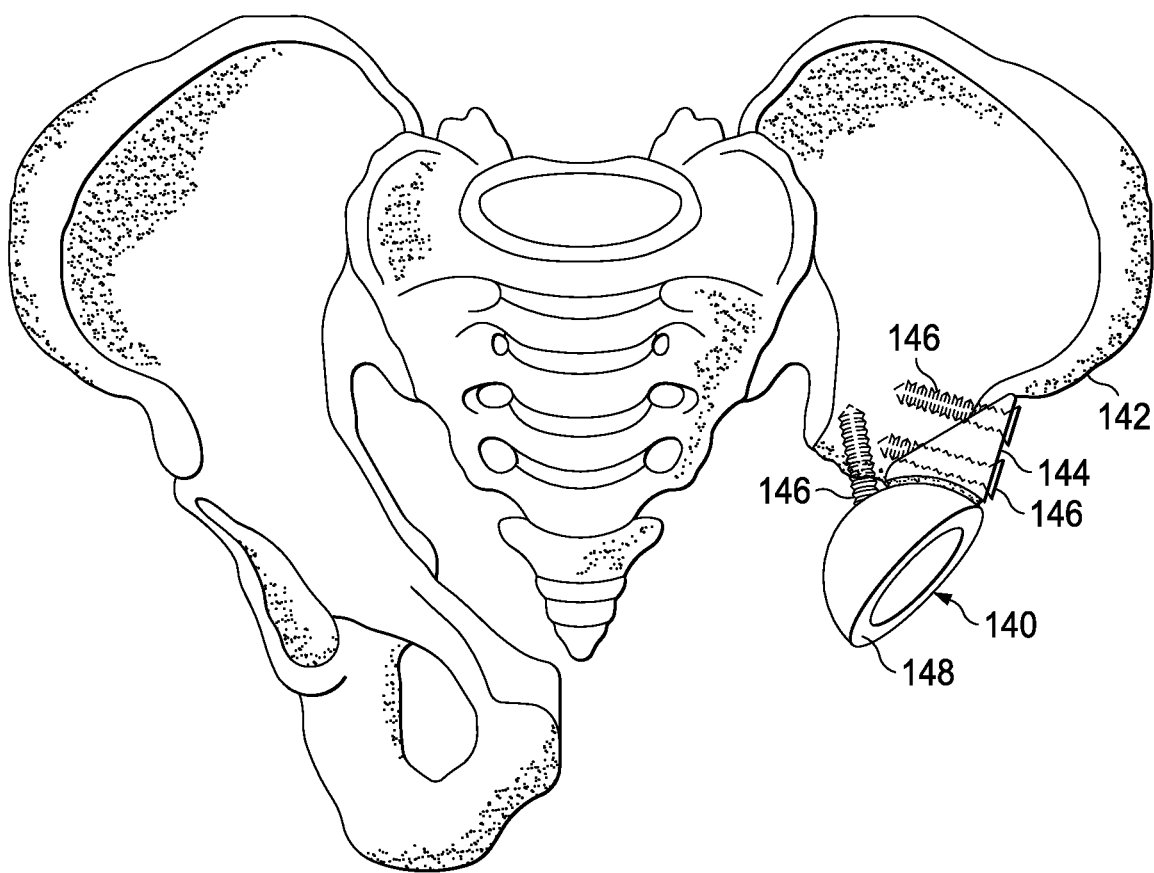
FIG. 15 is a diagram illustrating a plurality of conventional medical devices secured to bone of a patient.

To further secure the surgical implant 20 to the bone 90, one or more surgical screws 94 may be secured through one or more of the apertures 40. In each of the surgical procedures illustrated by FIGS. 10 and 11, the surgeon has elected to utilize only one of the surgical screws 94 via posterior placement of the surgical screw 94 through the aperture 40-4 to further secure the surgical implant 20 to the bone 90. The surgical implant 20 advantageously allows the surgeon to access a more solid portion of the bone 90 relative to other portions of the bone 90 adjacent to the surgical implant 20.

As illustrated, the surgical implant 20 is securely mounted to the bone 90 without any intermediate device, adhesive, or other element. In other words, there is no intermediate device, adhesive, or other element between the surgical implant 20 and the bone 90. Thus, the surgical implant 20 is operable to transmit and/or distribute any force received thereon, e.g., via another implant secured to the interior surface 26 of the cavity 30, directly to the bone 90 via at least the stem 60 of the surgical implant 20. For instance, the surgical implant 20 is operable to distribute force received from intact iliac bone when the patient ambulates such that the surgical implant 20 shares the load with the bone 90.

It has been discovered that the efficient transfer and/or distribution of force to the bone 90, as advantageously provided by the surgical implant 20, causes the human body to more readily receive the surgical implant 20, which facilitates growth of the bone 90 around the stem 60 and around and into the cup 22. Indeed, when the body receives forces transferred and/or distributed by the surgical implant 20, such is interpreted by the body as a potent biological signal, which causes the body to make the bone 90 denser. In this manner, growth of the bone 90 around the surgical implant 20 is facilitated. Once the cup 22 has been incorporated into the bone 90, the surgical screw 94 becomes an inert piece of metal, with a majority of the load shared between the surgical implant 20 and the bone 90.

The surgical implant 20 is formed from a mono block, i.e., a unitary piece of material, such as stainless steel, a resin material, or the like. In this manner, the cup 22 and the stem 60 are made of the same material. The stem 60 is formed to have one of a plurality of lengths, i.e., 40 mm, 45 mm, or 50 mm. The stem 60 is formed to be tapered in a direction from the point 66 toward the points 68 such that a width at the points 68 is X mm and a width at a point 40 to 100 mm from the point 66 is X−2 mm.

In the exemplary embodiment the width at the points 68 is 8 mm or 10 mm and the width at the point 40 to 100 mm from the point 66 is 6 mm or 8 mm. The troughs 70 are formed to have a maximum depth of 4 mm and a minimum depth of 0 mm at the points 68. After formation of the surgical implant 20, an entirety of the surgical implant 20 is coated via hydroxyapatite (HA) or other like coating, e.g., via a spray-coating process or a dipping process. It is foreseen that only the stem 60 may be coated with HA without deviating from the scope of the present inventive concept.

Figure 2:
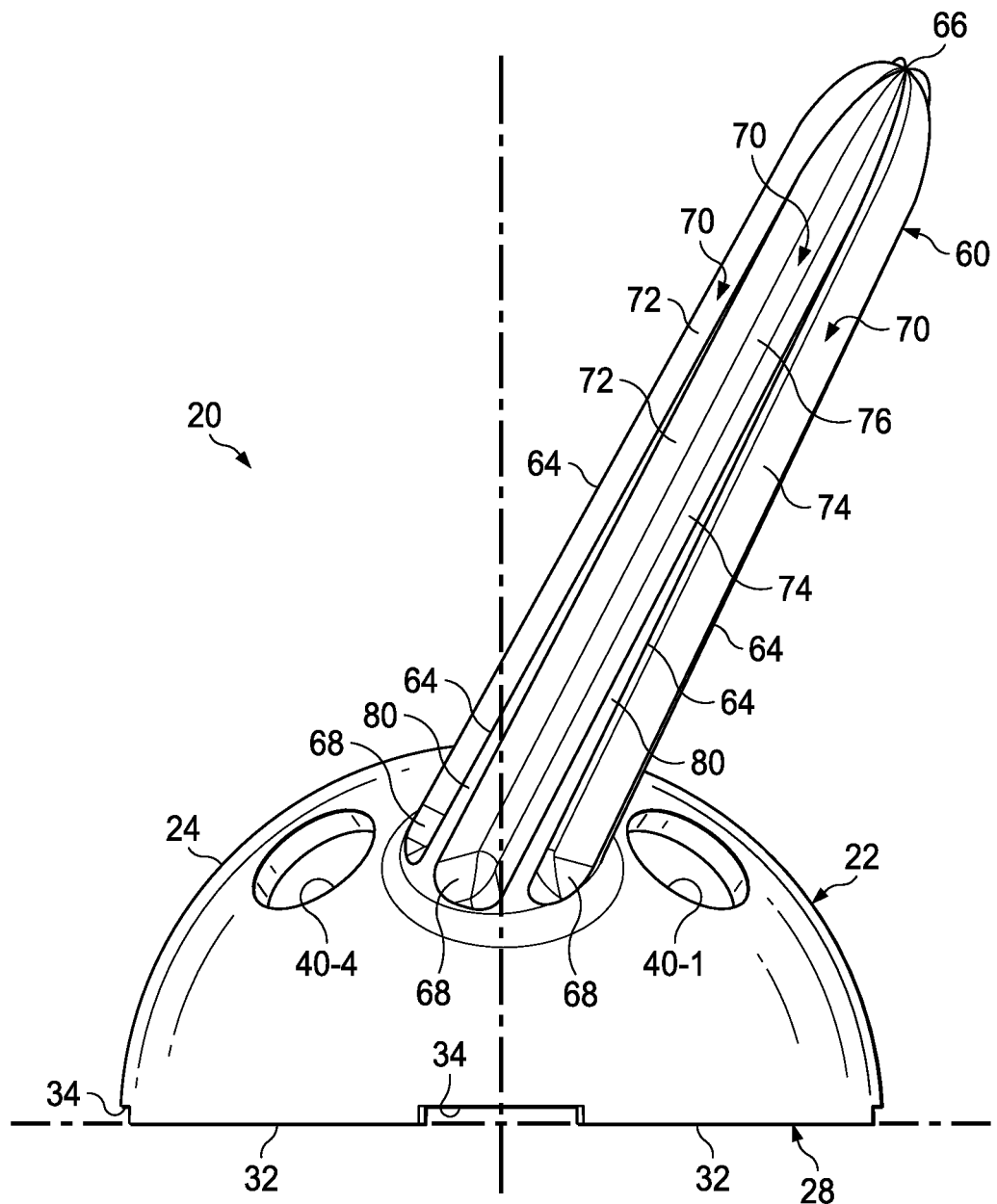
FIG. 2 is a front side elevation view of the surgical implant of FIG. 1.
Figure 3:
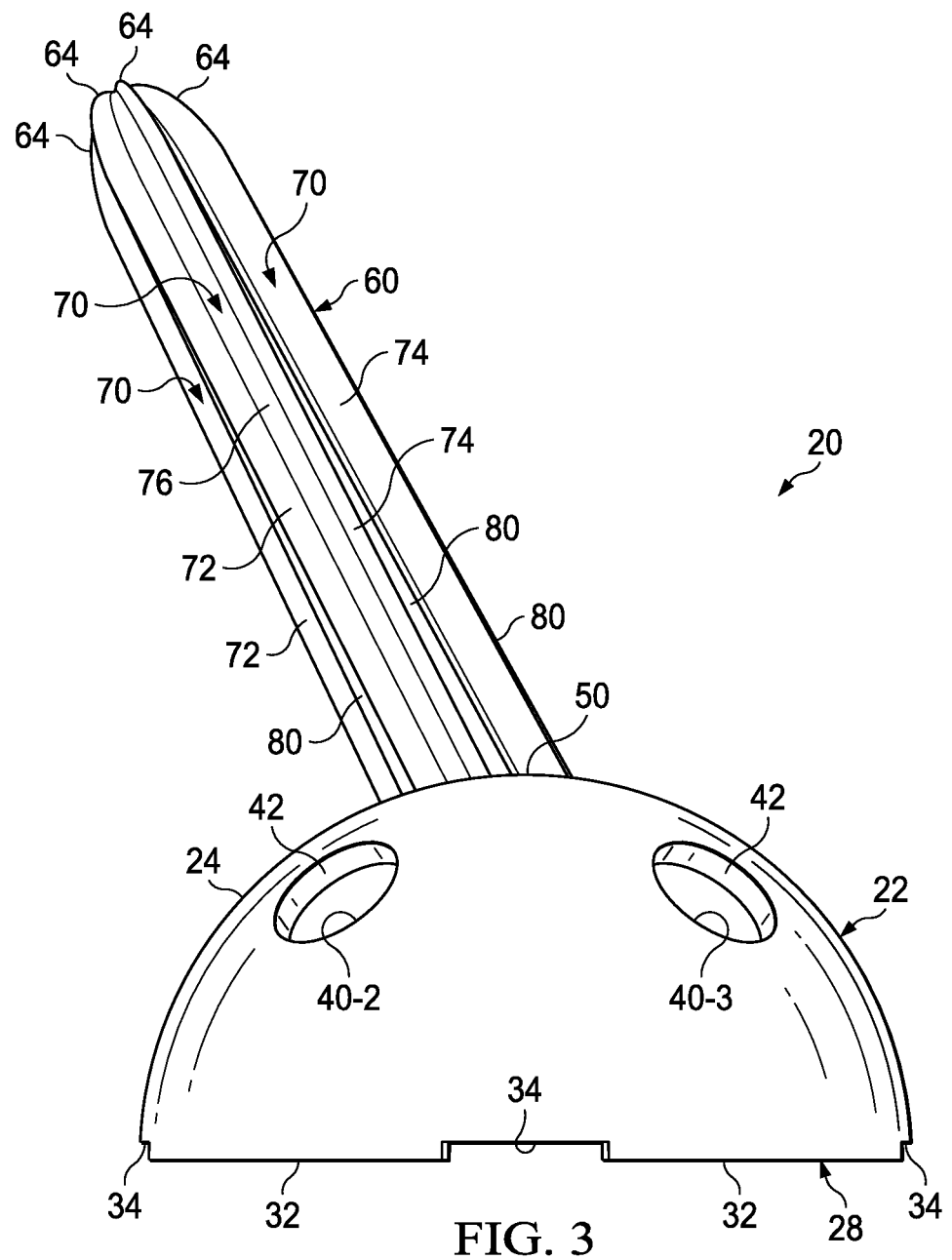
FIG. 3 is a rear side elevation view of the surgical implant of FIG. 1.
Figure 4:
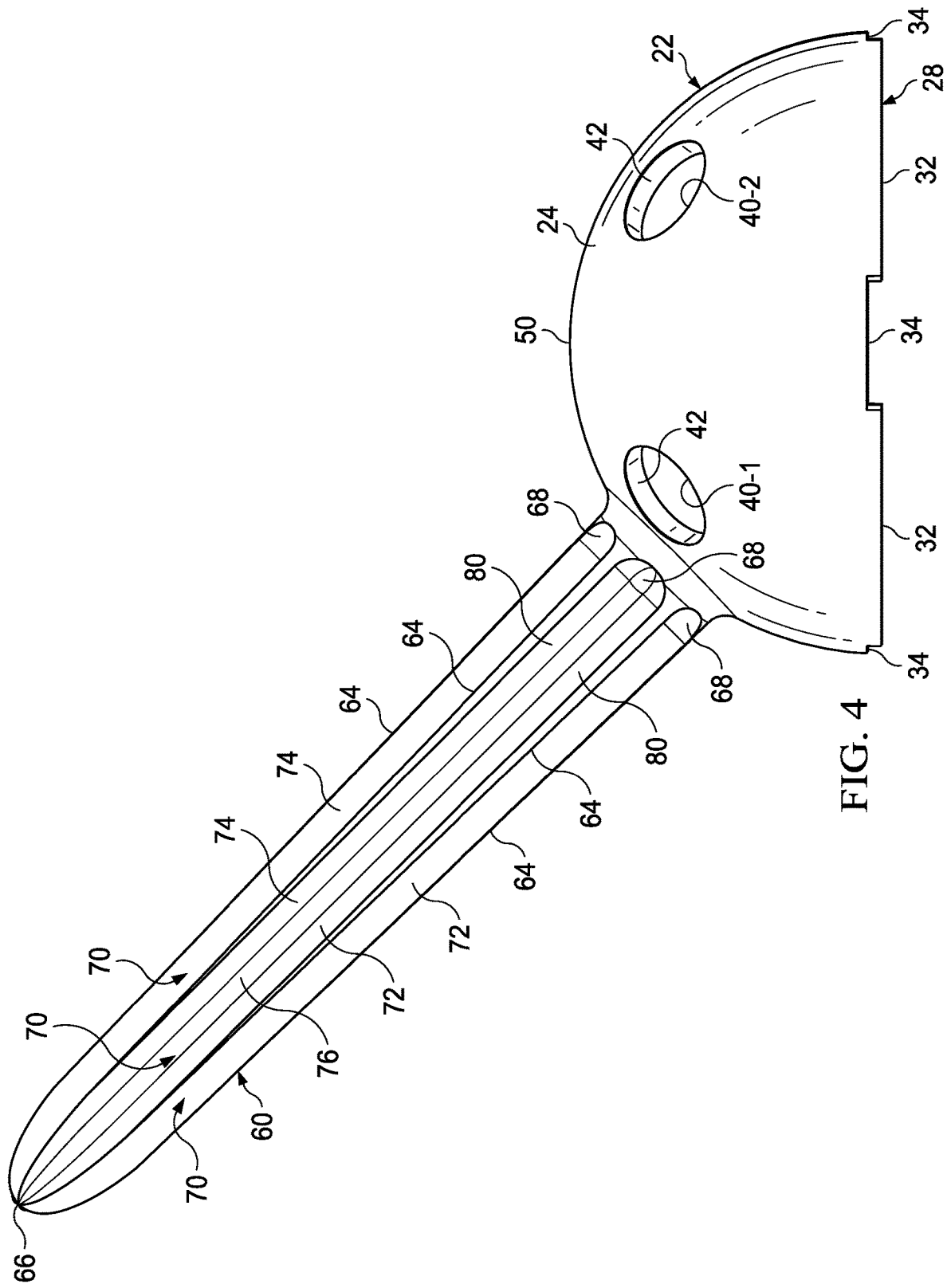
FIG. 4 is a left side elevation view of the surgical implant of FIG. 1.
Figure 6:
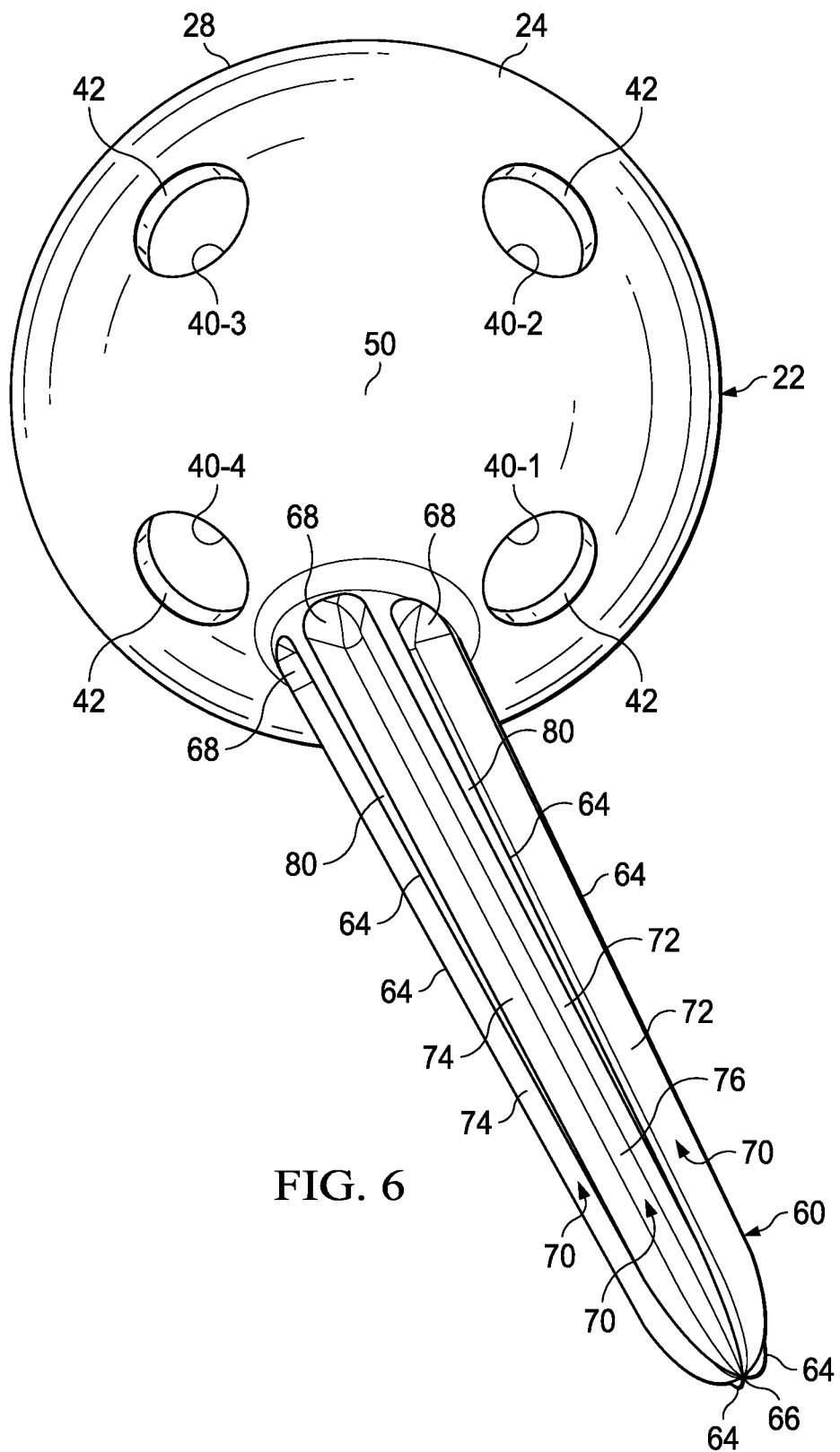
FIG. 6 is a top plan view of the surgical implant of FIG. 1.
Figure 7:
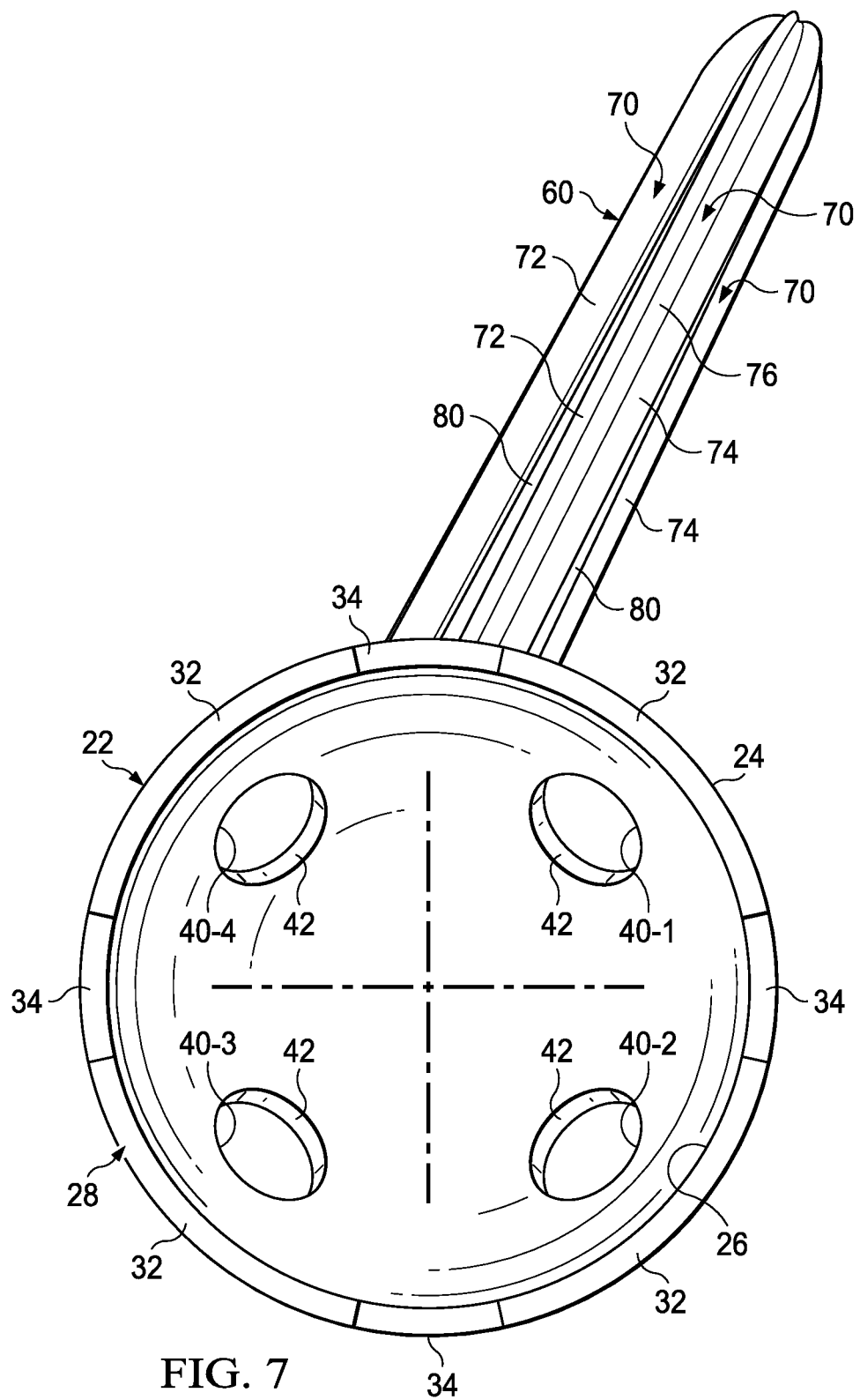
FIG. 7 is a bottom plan view of the surgical implant of FIG. 1.
Figure 8:
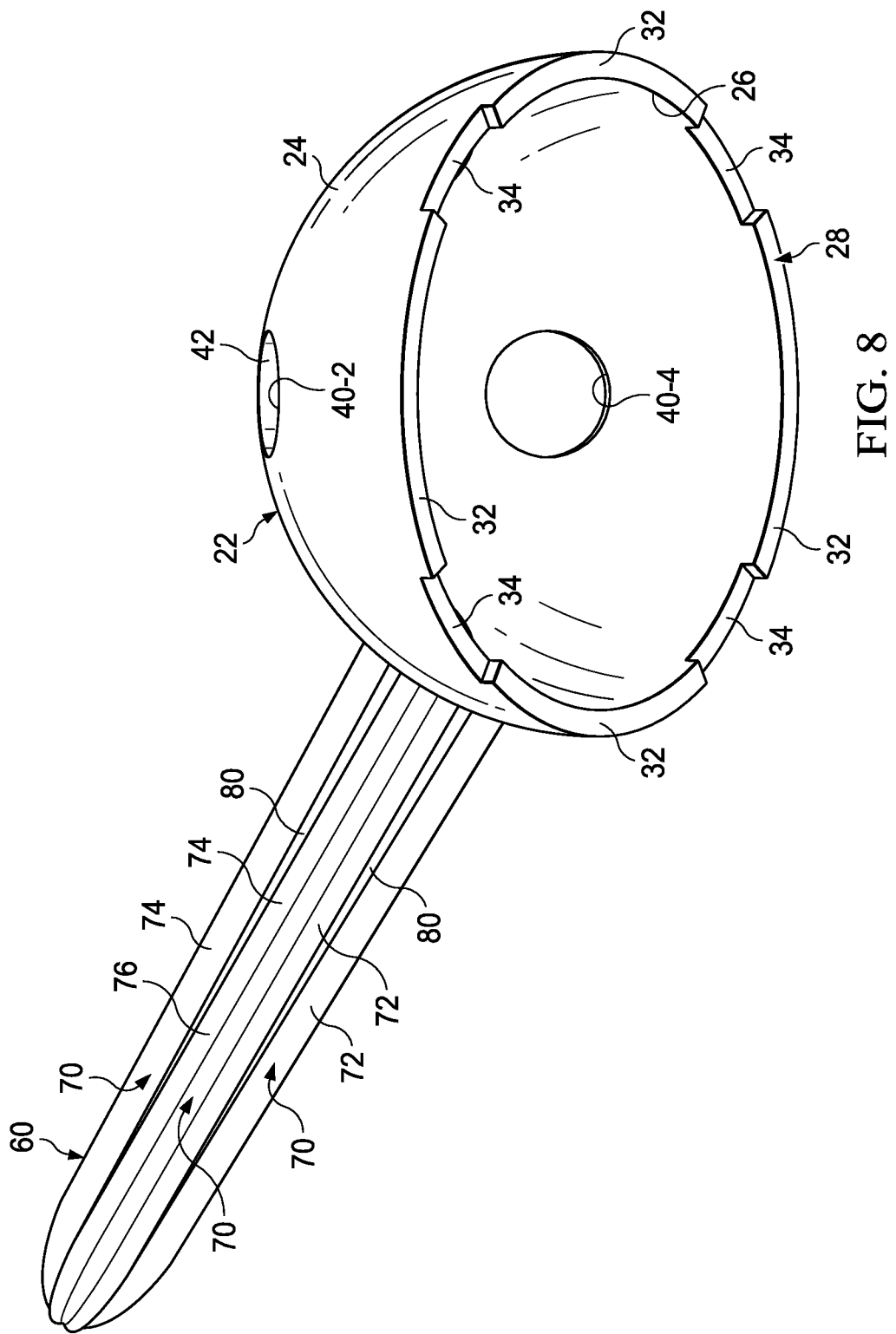
FIG. 8 is a bottom, left, rear perspective view of the surgical implant of FIG. 1.

The stem 60 is formed to extend from the cup 22 at a forty-five degree angle thereto, as illustrated by FIGS. 4 and 5. The stem 60 is formed to have a twenty degree anteverted orientation, i.e., an anterior angulation or "tipping forward," relative to the plane defined by the rim 28. As illustrated by FIG. 2, instead of extending straight from the cup, i.e., at zero degrees, the stem 60 extends from the cup 22 at a twenty degree angle thereto. As illustrated by FIG. 6, the stem 60 and the apertures 40 are equally spaced at a distance between the center point 50 and the rim 28.

The stem 60 is formed to extend from and be oriented with respect to the cup 22 based on whether the surgical implant 20 is to be used on a left side of the patient, i.e., a left acetabulum, or a right side of the patient, i.e., a right acetabulum, for reconstruction of a segmental acetabular defect with pelvic discontinuity. Thus, the surgical implant 20 may be formed to have a mirror image of the surgical implant 20, as illustrated by FIGS. 1-8, which is formed for use with a left acetabulum.

Accordingly, the present inventive concept maximizes transmission of force received from the medical device 20 to the bone 90, simplifies the surgical procedure required to use the medical device, does not allow forces to be transmitted between multiple implants, is readily accepted by surrounding bone, allows growth of bone in and around the device, has a simple design that is easy to use, has a reproducible technique for implantation, minimizes surgical exposure and stripping of the bone, and does not prolong recovery time or expenses of a patient, and does not increase the risk of repeat revision surgery

Having now described the features, discoveries and principles of the general inventive concept, the manner in which the general inventive concept is constructed and used, the characteristics of the construction, and advantageous, new and useful results obtained; the new and useful structures, devices, tools, elements, arrangements, parts and combinations, are set forth in the appended claims.

It is also to be understood that the following claims are intended to cover all of the generic and specific features of the general inventive concept herein described, and all statements of the scope of the general inventive concept which, as a matter of language, might be said to fall there between.

What is claimed is:

1. A surgical implant comprising:
   a hemispherical cup having (i) a bone-abutment exterior surface defining a convex side of the cup, (ii) an interior surface defining a concave side of the cup with a cavity, and (iii) a circumferential rim extending between the bone-abutment exterior surface and the interior surface;
   at least one aperture defined by a circumferential surface extending between the bone-abutment exterior surface and the interior surface, the at least one aperture operable to receive a screw therethrough; and
   a stress-diffusion element extending directly from the bone-abutment exterior surface of the cup at an anteverted orientation to the cup, wherein the cup and the stress-diffusion element are monolithic.

2. The surgical implant of claim 1,
   wherein,
   the rim extends along a plane and defines a circle with a first center point,
   the bone-abutment exterior surface of the cup defines a second center point, and
   a line between the first center point and the second center point extends perpendicular to the plane.

3. The surgical implant of claim 2,
   wherein,
   the stress-diffusion element is a stem extending from the cup.

4. The surgical implant of claim 3,
   wherein,
   the stem includes a base formed on the bone-abutment exterior surface of the cup and spaced from the second center point.

5. The surgical implant of claim 4,
   wherein,
   the base is centrally formed between the second center point and a closest portion of the rim.

6. The surgical implant of claim 4,
   wherein,
   the base is centrally formed between the at least one aperture and another aperture extending between the bone-abutment exterior surface and the interior surface.

7. The surgical implant of claim 3,
   wherein,
   the stem includes a plurality of longitudinal flutes, each of the plurality of longitudinal flutes extending along an entirety of the stem with (i) distal ends of the plurality of longitudinal flutes adjoining at a common point, and (ii) proximal ends of the plurality of longitudinal flutes tapering at separate points.

8. The surgical implant of claim 7,
   wherein,
   adjacent ones of the plurality of longitudinal flutes are spaced from each other by one of a plurality of troughs, and
   each of the plurality of troughs includes sidewalls and a bottom wall.

9. The surgical implant of claim 8,
   wherein,
   each of the plurality of troughs includes an increasing depth along the stem.

10. The surgical implant of claim 8,
    wherein,
    each of the plurality of longitudinal flutes includes a plateau along a portion thereof with an increasing width along the stem.

11. The surgical implant of claim 8,
    wherein,
    each of the plurality of longitudinal flutes surrounds a portion of the adjacent ones of the plurality of troughs.

12. The surgical implant of claim 8,
    wherein,
    the sidewalls of each of the plurality of troughs converge.

13. The surgical implant of claim 8, wherein,
   the at least one aperture includes four apertures arranged equidistant relative to each other along the cup.

14. The surgical implant of claim 2, wherein,
   the stress-diffusion element extends from a point on the bone-abutment exterior surface, and
   the point is spaced from the second center point.

15. The surgical implant of claim 14, wherein,
   the stress-diffusion element extends from the cup at forty-five degrees relative to the plane, and
   the anteverted orientation of the stress-diffusion element relative to the cup is twenty degrees relative to the line.

16. The surgical implant of claim 2, wherein,
   the at least one aperture is a plurality of apertures,
   the plurality of apertures are equidistant relative to each other along the cup,
   the stress-diffusion element extends from a point on the bone-abutment exterior surface, and
   the point is spaced from the second center point and between the plurality of apertures.

17. The surgical implant of claim 1, wherein,
   the stress-diffusion element includes a plurality of longitudinal flutes, and
   each of the plurality of longitudinal flutes extending along a substantial portion of the stress-diffusion element.

18. A surgical implant comprising:
   a hemispherical cup having (i) a bone-abutment exterior surface defining a convex side of the cup, (ii) an interior surface defining a concave side of the cup with a cavity, and (iii) a circumferential rim extending between the bone-abutment exterior surface and the interior surface, the rim extending along a plane and defining a circle with a first center point, the bone-abutment exterior surface of the cup defining a second center point, a line between the first center point and the second center point extending perpendicular to the plane;
   at least one aperture defined by a circumferential surface extending between the bone-abutment exterior surface and the interior surface, the at least one aperture operable receive a screw therethrough; and
   a stress-diffusion element extending (i) directly from the bone-abutment exterior surface of the cup, (ii) at an anteverted orientation to the cup, and (iii) from a third point on the cup, the third point spaced from the second center point, wherein the stress-diffusion element and the hemispherical cup are monolithic.

19. A surgical implant comprising:
   a hemispherical cup having (i) a bone-abutment exterior surface defining a convex side of the cup, (ii) an interior surface defining a concave side of the cup and a cavity, and (iii) a circumferential rim extending between the bone-abutment exterior surface of the cup and the interior surface of the cup;
   at least one aperture having a circumferential surface extending between the bone-abutment exterior surface of the cup and the interior surface of the cup; and
   a stress-diffusion element extending directly from the bone-abutment exterior surface of the cup at an anteverted orientation to the cup, the stress-diffusion element and the cup being monolithic.

\* \* \* \* \*